(12) United States Patent
Thierauf

(10) Patent No.: US 6,918,482 B2
(45) Date of Patent: Jul. 19, 2005

(54) DEVICE AND METHOD FOR VERIFYING THE AUTHENTICITY OF BANKNOTES

(75) Inventor: Klaus Thierauf, Munich (DE)

(73) Assignee: Giesecke & Devrient GmbH, Munich (DE)

( * ) Notice: Subject to any disclaimer, the term of this patent is extended or adjusted under 35 U.S.C. 154(b) by 183 days.

(21) Appl. No.: 10/148,176

(22) PCT Filed: Nov. 30, 2000

(86) PCT No.: PCT/EP00/12055

§ 371 (c)(1),
(2), (4) Date: Aug. 20, 2002

(87) PCT Pub. No.: WO01/41079

PCT Pub. Date: Jun. 7, 2001

(65) Prior Publication Data

US 2003/0039359 A1 Feb. 27, 2003

(30) Foreign Application Priority Data

Dec. 3, 1999 (DE) .......................... 199 58 048

(51) Int. Cl.⁷ ..................... G07K 7/015; G07K 9/00
(52) U.S. Cl. .................. 194/207; 209/534; 382/135
(58) Field of Search .................. 194/207, 206, 194/205, 302; 382/135; 209/534

(56) References Cited

U.S. PATENT DOCUMENTS

| 3,946,203 A | | 3/1976 | Hecht et al. ........... 235/61.11 E |
| 4,202,491 A | | 5/1980 | Suzuki ..................... 235/491 |
| 4,592,090 A | * | 5/1986 | Curl et al. ................. 382/135 |
| 4,722,607 A | | 2/1988 | Anselment et al. ......... 356/417 |
| 5,476,169 A | * | 12/1995 | Takarada et al. ............. 194/207 |
| 5,574,790 A | * | 11/1996 | Liang et al. ................... 283/89 |
| 5,666,417 A | * | 9/1997 | Liang et al. ................... 283/92 |
| 5,912,982 A | | 6/1999 | Munro et al. ................ 382/135 |
| 5,915,518 A | | 6/1999 | Hopwood et al. ............ 194/207 |
| 5,960,103 A | | 9/1999 | Graves et al. ................ 382/135 |
| 6,101,266 A | * | 8/2000 | Laskowski et al. .......... 382/135 |
| 6,297,509 B1 | | 10/2001 | Lipkowitsch et al. ..... 250/461.1 |

FOREIGN PATENT DOCUMENTS

| GB | 2018483 | | 10/1979 | ............ G06K/9/00 |
| WO | WO 94/16412 | * | 7/1994 | ............ G07D/7/00 |
| WO | WO 95/19605 | | 7/1995 | ............ G06K/7/12 |

* cited by examiner

Primary Examiner—Donald P. Walsh
Assistant Examiner—Mark J. Beauchaine
(74) Attorney, Agent, or Firm—Bacon & Thomas, PLLC

(57) ABSTRACT

An apparatus and method for testing the authenticity of bank notes are proposed.

The apparatus includes a light source for emitting light suitable for exciting fluorescent light in a bank note to be checked, and a fluorescence detector for detecting the fluorescent light emitted by the bank note to be checked. According to the invention it is provided that the light source is a light-emitting diode and the light-emitting diode is formed to emit light containing ultraviolet light at least in a partial spectral region. This makes it possible in particular to obtain a compact structure of the apparatus.

The method involves exciting and detecting fluorescent light in the bank note to be checked and comparing the detected fluorescent light with a predefined threshold value. According to the invention it is provided that the detected fluorescent light is reduced by the ambient light detected with the light source switched off. This permits the elimination of measuring inaccuracies at the same time as simple operation.

25 Claims, 2 Drawing Sheets

DEVICE AND METHOD FOR VERIFYING THE AUTHENTICITY OF BANKNOTES

This invention relates to an apparatus and method for testing the authenticity of bank notes according to the preambles of claims 1 and 15.

Counterfeit bank notes are usually printed on customary paper containing optical brighteners. In contrast, the paper of authentic bank notes is generally free from optical brighteners. Detection of optical brighteners in a bank note can thus serve as a sign of the presence of a forgery. Optical brighteners are normally detected by irradiating the bank note to be checked with ultraviolet (UV) light. A counterfeit bank note printed on brightener-containing paper can be recognized since the bank note shows visible fluorescence in the irradiated area.

In the apparatuses and methods for testing the authenticity of bank notes described in the patent U.S. Pat. No. 5,640,463 the bank notes to be checked are illuminated with light from a IN light source and both the UV light reflected by the bank note to be checked and the fluorescent light emitted thereby are measured and compared with the values measured on an authentic bank note. The UV light source used is a fluorescent lamp.

However, the use of fluorescent lamps has various disadvantages. In particular, a compact structure of such an apparatus can hardly be realized since the shape and size of customary fluorescent lamps, e.g. a rod shape with a typical length of about 5 cm, prescribe a minimum size of the total apparatus. In addition, the light emitted by fluorescent lamps has not only UV components but also components in the visible and infrared spectral regions. This can lead to undesirable heating of the apparatus. Therefore, suitable cooling of the apparatus is necessary in many cases. Last but not least, high voltage is required for operating UV fluorescent lamps, which requires additional effort compared to the low voltage supply typically used in many transport or checking devices in bank note processing machines, and also favors the occurrence of disturbing voltages.

In known authenticity testing methods according to the prior art, measuring inaccuracies due e.g. to aging, soiling or ambient light are compensated by repeated reference measurements on reference documents, e.g. authentic and possibly new bank notes. This is awkward and time-consuming, however, since to take a reference measurement the actual checking operation must be interrupted each time for the corresponding reference documents to be inputted. Due to this fact, reference measurements can only be taken at relatively long time intervals, e.g. after a relatively large number of tested bank notes, since otherwise authenticity testing as a whole would be too time-intensive. Time-variant influences, e.g. due to ambient light and dark current in the detectors, can thus not be fully taken into account.

It is the problem of the present invention to state an apparatus for authenticity testing which is of compact construction and allows simple and reliable operation.

This problem is solved according to the invention by the apparatus and method according to claims 1 and 15.

The inventive apparatus develops the prior art in such a way that the light source used is a light-emitting diode and the light-emitting diode is formed to emit light containing ultraviolet light at least in a partial spectral region. Since light-emitting diodes generally have much smaller component sizes than the UV fluorescent lamps hitherto used, a compact structure of the inventive apparatus is possible. This permits a space-saving arrangement of a plurality of different sensors within a very small space to be realized, as is required in particular in bank note processing machines of small overall size. In addition, light-emitting diodes are more cost-effective than the UV fluorescent lamps hitherto used. The maximum operating lifetime of the provided light-emitting diodes is furthermore generally much longer than with UV fluorescent lamps. Thus, UV fluorescent lamps must be replaced after a maximum operating lifetime of typically less than 3000 hours, whereas the inventively provided light-emitting diodes have substantially longer maximum operating lifetimes. Unlike UV fluorescent lamps, light-emitting diodes can furthermore be switched on and off fast without any additional special circuit complexity. When used for testing the authenticity of bank notes, light-emitting diodes can therefore be operated in clocked fashion, or switched off for fashion, or switched off for a short time if for example the checking operation of one bank note is completed and the next bank note to be checked is not yet available or the bank note processing machine is stopped for a short time, e.g. to remove a jam. Temporarily switching off the light-emitting diode during operation further increases its maximum operating lifetime over UV fluorescent lamps. Further, the emission spectrum of the provided light-emitting diodes has very slight or no infrared components compared to the TV fluorescent lamps hitherto used. This avoids undesirable heating of the apparatus. This is the case in particular when a light-emitting diode is used whose emission spectrum has a peak in the ultraviolet spectral region.

According to a preferred development of the invention, a monitor detector is provided in addition to the fluorescence detector for detecting at least part of the light emitted by the light-emitting diode. The monitor detector measures the light intensity of the light-emitting diode in the course of its operating lifetime and delivers measured values that are used for correcting aging effects, in particular the decrease in intensity to be observed in the provided light-emitting diodes.

In a further preferred embodiment of the inventive apparatus, a lock-in amplifier is provided for amplifying output signals from the fluorescence detector and/or monitor detector. Lock-in amplifiers are used in the measurement and processing of very weak analog signals, whereby the signal background is very greatly suppressed. With a lock-in amplifier, the modulated output signal from a detector is amplified and demodulated in a synchronous demodulator with a standardized reference signal of the same modulation frequency. In a low-pass filter the high-frequency components are then filtered out. The resulting signal obtained is proportional to the amplitude of the amplified emitted fluorescent light or the reflected excitation light. Since the use of a lock-in amplifier is suitable in particular for amplifying very weak output signals from the fluorescence or monitor detector, it permits very weak fluorescent light or light emitted by the light source to be measured with high accuracy. This is of advantage especially when the intensity of the light source decreases in the course of its operating lifetime and the fluorescent light excited in the bank note to be checked consequently becomes weaker. The property of amplifying weak output signals also plays an impor-important role especially when the light-emitting diode used has an emission spectrum with only slight spectral components in the ultraviolet spectral region. This can be the case for example when a light-emitting diode emitting mainly in the visible spectral region and emitting little light in the ultraviolet spectral region is used instead of a UV light-emitting diode.

The inventive method is characterized substantially as follows. A partial area of the bank note to be checked is illuminated with the light of the light-emitting diode. The fluorescence detector is used to measure the fluorescent light emitted by the partial area and generate a first measured value. Additionally the fluorescence detector is used to measure with the light-emitting diode switched off and generate a second measured value. The first measured value is then corrected with the second measured value, e.g. by subtraction, and the thus corrected measured value is compared with a predefined threshold value. Measurement with the light-emitting diode switched off can generally also be done prior to measurement with the light-emitting diode switched on.

This method makes it possible to eliminate in a simple way any falsification by ambient light of the fluorescent light to be detected, since no measurement on reference documents is required but only a "dark measurement" to be simply realized by switching off the light-emitting diode. In particular this makes it possible to take a "dark measurement" before or after each actual fluorescence measurement without increasing the operative effort. Ambient light refers here to artificial or natural room light and light from other measuring devices in the immediate surroundings of the apparatus. Ambient light can pass into the detection area of the fluorescence detector directly or indirectly, e.g. by reflection on optical components or the bank note. The inventive method furthermore eliminates falsification of the measurement due to dark currents typically occurring with photodiodes, which flow through the detector even when no light is detected.

In a preferred embodiment of the inventive method, it is provided that the first measured value generated with the illumination switched on is corrected with the second measured value generated with the illumination switched off by lock-in amplifica-amplification of an output signal generated by the fluorescence detector. The light-emitting diode is switched on and off periodically by a suitable voltage source, e.g. a frequency generator. This permits detection of even low intensities of the fluorescent light emitted by the bank note and detected by the fluorescence detector. This is of importance in particular when a counterfeit bank note to be checked contains only small traces of optical brighteners and the fluorescent light emitted thereby consequently has only a low intensity. Lock-in amplification of the output signal is also of advantage when the intensity of the light emitted by the light source becomes weaker in the course of the operating lifetime and the excited fluorescence in the bank note is accordingly weak.

In a development of the method, it is provided that the corrected measured value or the threshold value is corrected with correction value K which takes account of the change of intensity of the light emitted by the light-emitting diode in the course of the operating lifetime of the light-emitting diode. This permits the influence of intensity fluctuations of the light-emitting diode to be eliminated, so that an intensity of the fluorescence of the bank note that is substantially independent of intensity fluctuations of the light exciting the fluorescence can be determined at any time within the operating lifetime.

A further aspect of the invention is that fluorescent light emitted by the bank note is measured with the light-emitting diode switched on and phosphorescent light emitted by the bank note with the light-emitting diode switched off. The measured fluorescent and phosphorescent light of the bank note is then used for authenticity testing. Measurement is preferably done with the fluorescence detector in each case. The light-emitting diode is operated in pulsed fashion, in particular by periodic pulses. This method variant is suitable for testing the authenticity of bank notes that show not only fluorescence but also phosphorescence. If the fluorescence and phosphorescence properties of the bank note are known, the presence of certain substances in the bank note can then be inferred, for example. Such separate measurement of the fluorescent and phosphorescent light emitted by the bank note can be realized very simply using a light-emitting diode as a light source, since light-emitting diodes are particularly suitable for generating, in particular short, pulses.

In the following, the invention will be explained in more detail with reference to examples shown in figures, in which.

Figure 1:
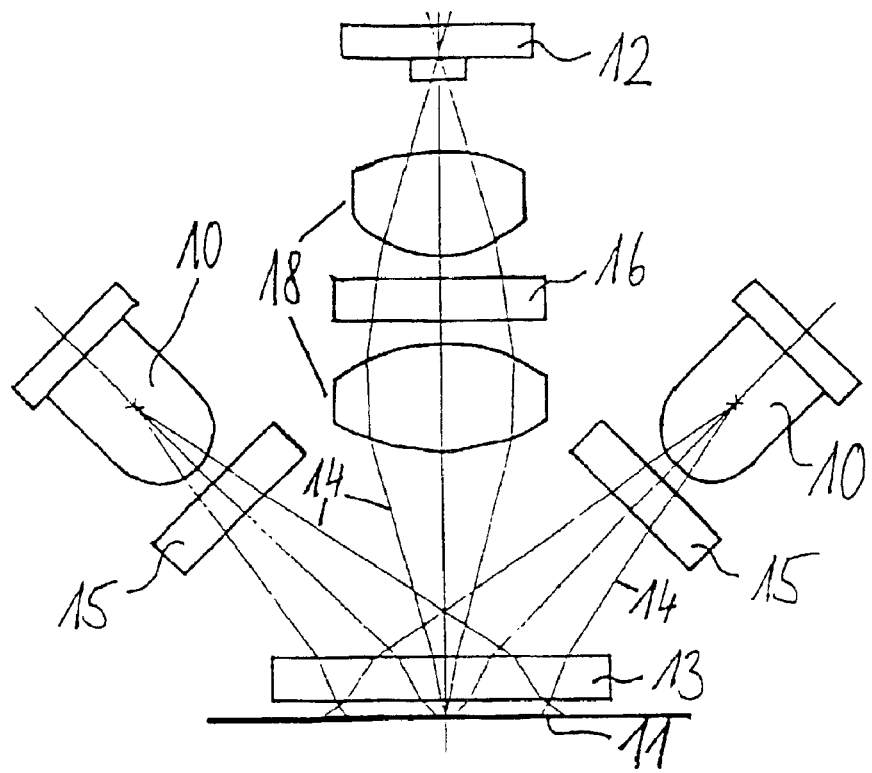
FIG. 1 shows the schematic structure of a first example with two light-emitting diodes and a fluorescence detector.

FIG. 1 shows the schematic structure of an example with two light-emitting diodes 10 and fluorescence detector 12. The light emitted by light-emitting diodes 10 has ultraviolet components that are used for exciting fluorescent light in bank note to be checked 11. These may be for example light-emitting diodes having an emission spectrum with a peak in the ultraviolet spectral region. The emission peak of typical light-emitting diodes is about 370 nanometers and has a half-value width of about 12 nanometers. Alternatively it is also possible for the light-emitting diodes to have an emission peak in the visible spectral region, e.g. at about 430 nanometers, but also emit sufficiently high components of ultraviolet light. In both cases, particularly the latter, it may be necessary to select a certain spectral region from the emission spectrum of the light-emitting diodes for exciting fluorescent light in bank note to be checked 11. This is done by first filter 15 disposed before light-emitting diodes 10. Suitable filters typically have an edge at 400 nanometers and are impermeable to light with greater wave-lengths.

In order to guarantee that fluorescence detector 12 detects substantially the visible fluorescent light emitted by bank note 11, second filter 16 with suitable spectral transmission characteristics is mounted before fluorescence detector 12. A suitable filter typically has an edge at about 400 nanometers and is impermeable to light with smaller wavelengths.

Lens system 18 serves to collimate the fluorescent light emitted by bank note to be checked 11 onto fluorescence detector 12. Lens system 18 can furthermore serve to parallelize the fluorescent light passing through second filter 16. This is of importance when an interference filter is used as second filter 16, since a substantially parallel beam path prevents a shift of the filter edge on the interference filter. A screen (not shown) can fundamentally also be used instead of lens system 18 to minimize costs.

In the shown example, window 13 that is permeable at least to parts of the excitation light and the fluorescent light is provided between bank note to be checked 11, on the one hand, and light-emitting diodes 10 and fluorescence detector 12 including filters 15 and 16 and lens system 18, on the other hand. During the authenticity testing process, bank notes 11 can be transported with a suitable transport device parallel to window 13, window 13 also serving to protect the individual components of the apparatus from dust and other soiling.

As can be seen by schematically shown beam path 14, the light of light-emitting diodes 10 illuminates an extended partial area of bank note to be checked 11, i.e. the light of light-emitting diodes 10 is not focused on bank note 11.

However, it is fundamentally of advantage here to concentrate the light emitted by the light-emitting diodes, for example by convergent beams (not shown), since this obtains higher intensity of the excitation light on the illuminated partial area of bank note 11. At the same time, the fluorescent light excited in the illuminated partial area of bank note 11 is detected by fluorescence detector 12 integrally, i.e. the light emitted by a finite area is measured. Nonfocusing illumination of bank note 11 and integral detection of the fluorescent light over a certain surface area cause the fluorescence properties of bank note 11 to be averaged, so that local irregularities such as soil particles or folds have a less disturbing effect than is the case with focused illumination. Typical sizes of the surface areas on bank note 11 are about 0.4 square centimeters for the illuminated partial area and about 0.4 square centimeters for the area over which the fluorescent light is detected integrally.

Figure 2:
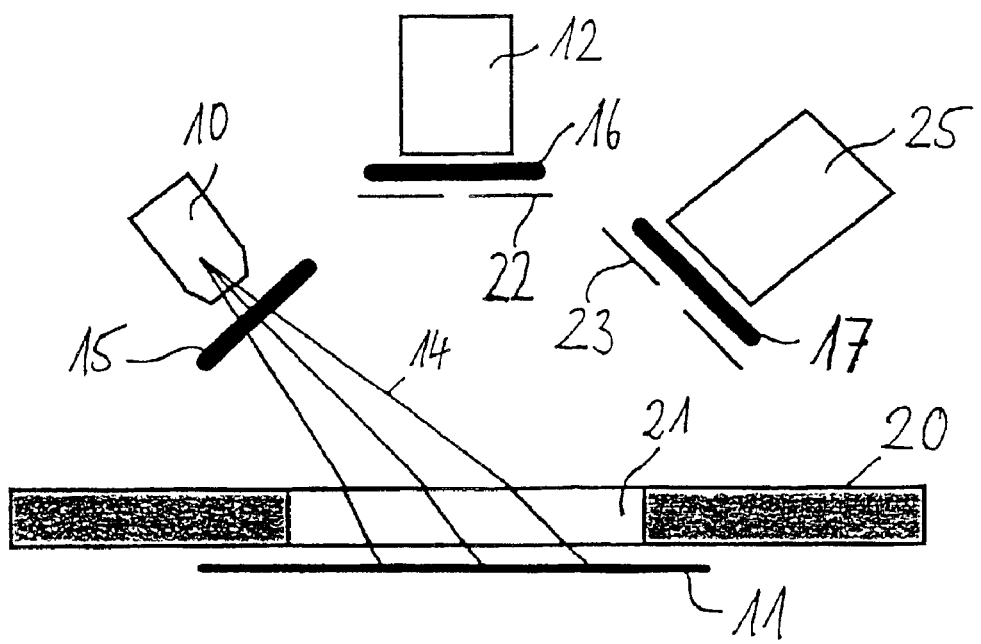
FIG. 2 shows the schematic structure of a further example with a light-emitting diode, a fluorescence detector and a monitor detector.

FIG. 2 shows the schematic structure of a further example. Light-emitting diode 10 provided with first filter 15 is used for illuminating bank note to be checked 11 11 which is transported parallel to transport plate 20. Transport plate 20 is opaque in this example and has three-dimensional partial area 21 which is permeable at least to spectral components of both the excitation light and the fluorescent light emitted by bank note 11. Transport plate 20 can be part of a housing in which the total apparatus is integrated, and thus serves to protect the individual components of the apparatus from dust and other soiling. As can be seen by schematically indicated beam path 14, the light of light-emitting diode 10 is also unfocused when hitting bank note 11 in this example. The typical size of the surface area of said illuminated partial area on bank note 11 is about 0.4 square centimeters.

When passing three-dimensional partial area 21 of transport plate 20, bank note 11 is illuminated by the ultraviolet components of the excitation light emitted by light-emitting diode 10 including first filter 15. If optical brighteners are present in bank note 11, this excites fluorescence in the visible spectral region. The excited fluorescent light passes through three-dimensional partial area 21 of transport plate 20 and hits fluorescence detector 12 provided with second filter 16. For collimating the fluorescent light emitted by bank note 11 there is first screen 22 before detector 12. In this arrangement, fluorescent light is detected integrally over surface areas with typical sizes of under 1 square centimeter.

In this example, monitor detector 25 is provided for measuring the brightness of light-emitting diode 10. For this purpose, the light emitted by light-emitting diode 10 and spectrally filtered is reflected at least partly on transport plate 20 and/or on three-dimensional partial area 21 of transport plate 20 and detected by monitor detector 25. Part of the light emitted by light-emitting diode 10 can fundamentally also be coupled out by other suitable means, such as mirrors or optical fibers, and supplied to monitor detector 25.

In a further variant of this structure, it is provided that light-emitting diode 10, monitor detector 25 and first filter 15 are disposed such that the light emitted by light-emitting diode 10 is partly reflected on first filter 15 and reaches monitor detector 25. First filter 15 is inclined relative to the light beams coming from light-emitting diode 10 such that the light beams obliquely hitting first filter 15 can be partly reflected there and reach monitor detector 25. Monitor detector 25 is preferably disposed between light-emitting diode 10 and fluorescence detector 12 (not shown). This variant has the advantage that the light reflected by first filter 15 and hitting monitor detector 25 is not overlaid and thus falsified by scattered light components from bank note 11 or possibly soiled partial area 21 of transport plate 20. Coating the side of first filter 15 facing light-emitting diode 10 in addition prevents reflections on said side of the filter, so that only the side of first filter 15 facing away from light-emitting diode 10 reflects. This additionally takes account of changes in the transmission behavior of first filter 15. If e.g. the transmission of the filter decreases, the intensity of the UV light hitting bank note 11 decreases and the component of reflected light hitting monitor detector 25 is accordingly lower.

For beam collimation the shown example has second screen 23, and spectral filtering is effected by third filter 17 disposed before monitor detector 25. The intensity of light-emitting diode 10 is preferably measured here without a bank note, i.e. there is no bank note before transparent three-dimensional partial area 21. This prevents any light diffusely reflected by the bank note from hitting monitor detector 25 and falsifying the measurement of the instantaneous brightness of the light-emitting diode.

The detectors used are preferably photodiodes. Three-dimensional partial area 21 of transport plate 20, which is at least partly transparent to both excitation light and fluorescent light, is generally made of suitable glass material. Absorption edges of typical glass materials are under 350 nanometers so that the latter are permeable to light with greater wavelengths. Second filter 16 and third filter 17 can alternatively be firmly connected, e.g. vapor-deposited or glued, to particular detector 12 or 25.

The measurement of ambient light and fluorescent light can be performed several times on each bank note to be checked 11. For example, bank note 11 can be tested in a track measurement by transporting the bank note past partial area 21 of the transport plate and measuring it at certain distances. Typical track widths are about 6 millimeters, typical distances between measurements about 2 millimeters. The thus obtained values can then be averaged so as to generate a mean value that is a measure of the average fluorescence behavior of bank note 11. The mean value can be determined e.g. determined e.g. by arithmetic averaging of the values. Alternatively, the mean value can be determined from the individual values by using a so-called median filter that eliminates peak values from the series of individual values and thus "smoothes" the series.

The mean value can then be compared with the predefined threshold value. If the mean value is greater than the threshold value, this indicates a forgery.

With a periodic or pulsed voltage supply of light-emitting diode 10 and amplification of the output signal from fluorescence detector 12 with a lock-in amplifier, the fluorescent light is reduced by the components of the ambient light automatically, i.e. by the lock-in method itself, so that separate measurement of the ambient light is unnecessary.

Figure 3:
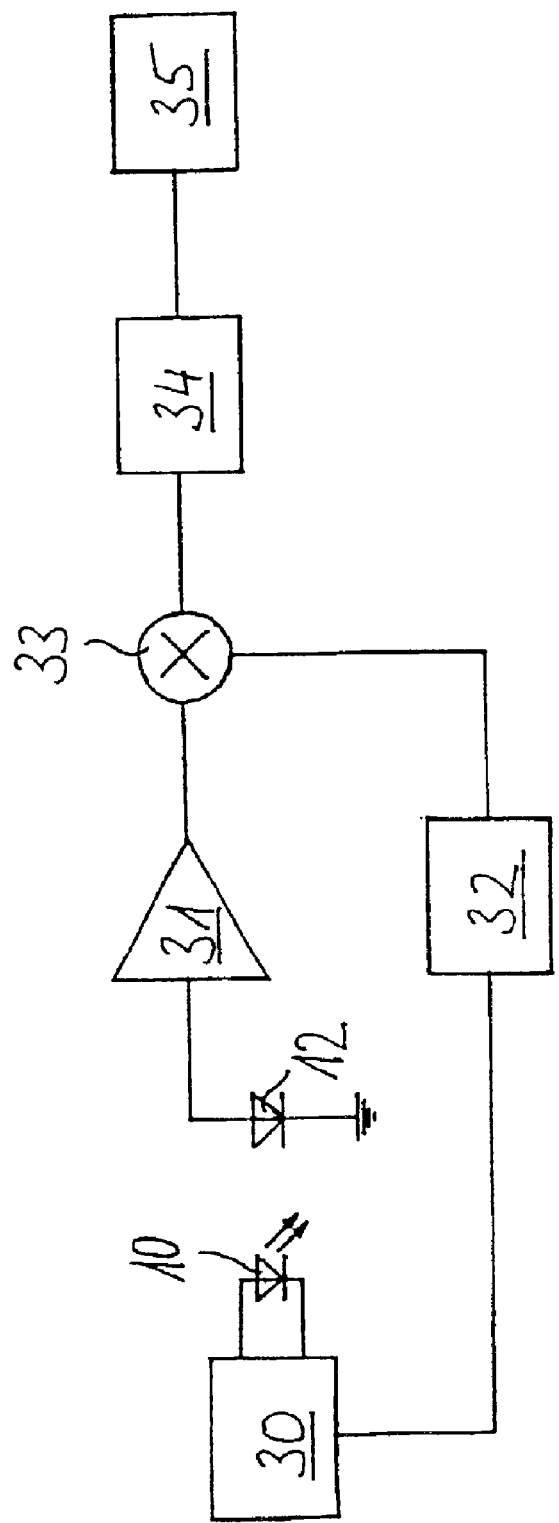
FIG. 3 shows a schematic circuit diagram of the inventively provided lock-in amplifier.

FIG. 3 shows a schematic circuit diagram of the inventively provided lock-in amplifier in connection with light-emitting diode 10 and fluorescence detector 12. Frequency generator 30 is connected with light-emitting diode 10. The fluorescent light excited in bank note 11 (not shown) by light from light-emitting diode 10 is detected by fluorescence detector 12 formed as a photodiode in this example. The output signal from fluorescence detector 12 is then amplified in transimpedance amplifier 31 and supplied to synchronous demodulator 33 together with a reference signal generated by frequency generator 30 and passed through phase shifter 32. The output signal from the synchronous demodulator is filtered in low-pass filter 34 and can be supplied to analogto-digital converter 35 for further processing. The schematic circuit explained can also be used for determining the brightness of light-emitting diode 10 with the aid of monitor detector 25. In this case, monitor detector 12 is simply connected or switched to transimpedance amplifier 31, instead of fluorescence detector 25.

The inventive method or its developments are preferably repeated at several places on the bank note. This makes the authenticity testing of bank notes safer and more reliable than with measurement at only one place on the bank note to be checked. The corrected measured values characterizing the fluorescence behavior of the bank note at individual places can then be averaged, for example to reduce any soiling effects at individual places on the bank note to be checked.

What is claimed is:

1. An apparatus for testing the authenticity of bank notes comprising:
    at least one light source for emitting light suitable for exciting fluorescent light in a bank note to be checked wherein the light source is a light-emitting diode arranged to emit light containing ultraviolet light at least in a partial spectral region;
    at least one fluorescence detector for detecting fluorescent light emitted by a bank note to be checked;
    at least one amplifying device arranged to amplify output signals from the at least one fluorescent detector and/or a monitor detector; the amplifying device being formed as a lock-in amplifier; and
    a transport plate disposed between the light-emitting diode and the fluorescence detector, and a bank note to be checked, the transport plate having at least one-three dimensional partial area permeable at least to a partial spectral region of the light emitted by the light-emitting diode and at least to a partial spectral region of the fluorescent light emitted by a bank note to be checked.

2. Apparatus according to claim 1, wherein the light-emitting diode has an emission spectrum with a peak in the ultraviolet spectral region.

3. Apparatus according to claim 1, wherein
    the light-emitting diode is arranged to emit light suitable for exciting fluorescent light in an extended partial area of a bank note to be checked, and
    the fluorescence detector is arranged for integral detection of the fluorescent light emitted by a bank note.

4. Apparatus according to claim 1, including a first filter arranged to filter light emitted by the light-emitting diode, the filter being permeable to a partial spectral region of the light emitted by the light-emitting diode and suitable for exciting fluorescent light in a bank note to be checked.

5. Apparatus according to claim 4, including a second filter arranged to filter the fluorescent light emitted by a bank note to be checked and to be detected by the fluorescence detector.

6. Apparatus according to claim 1, wherein the monitor detector is arranged to detect at least part of the light emitted by the light-emitting diode.

7. Apparatus according to claim 6, wherein the light-emitting diode, monitor detector and transport plate or first filter are disposed such that light emitted by the light-emitting diode is partly reflected on the transport plate or the first filter and reaches the monitor detector.

8. Apparatus according to claim 6, including a second screen arranged to collimate light emitted by the light-emitting di-diode and partly reflected on the transport plate onto the monitor detector.

9. Apparatus according to claim 6, including at least one amplifying device arranged to amplify output signals from the fluorescence detector and/or the monitor detector, the amplifying device being formed as a lock-in amplifier.

10. Apparatus according to claim 1, including a filter arranged to filter the light emitted by the light-emitting diode and partly reflected on the transport plate and to be detected by a monitor detector.

11. Apparatus according to claim 1, including a first screen arranged to collimate fluorescent light emitted by a bank note to be checked onto the fluorescence detector.

12. Apparatus according to claim 1, including a system of optical lenses arranged to collimate fluorescent light emitted by a bank note to be checked onto the fluorescence detector.

13. Apparatus according to claim 1, including a voltage source arranged to generate a voltage with periodic time behavior for supplying power to the light-emitting diode.

14. Use of the apparatus for testing the authenticity of bank notes according to claim 1, characterized by the steps of
    measuring fluorescent light emitted by the bank note to be checked with the fluorescence detector with the light-emitting diode switched on,
    measuring phosphorescent light emitted by the bank note to be checked with the fluorescence detector with the light-emitting diode switched off, and
    using the measured fluorescent and phosphorescent light of the bank note to be checked for authenticity testing.

15. Apparatus according to claim 1, including a filter arranged to filter the fluorescent light emitted by a bank note to be checked and to be detected by the fluorescence detector.

16. Apparatus according to claim 1, wherein the monitor detector is arranged to detect at least part of the light emitted by the light-emitting diode.

17. A method for testing the authenticity of bank notes comprising the steps of illuminating a bank note to be checked with ultraviolet light from a light source, measuring visible fluorescent light emitted by the bank note to be checked with a fluorescence detector, and comparing the measured fluorescent light with a predefined threshold value, comprising the following steps:
    a) illuminating at least a partial area of the bank note to be checked with light emitted by a light-emitting diode, said light containing ultraviolet light at least in a partial spectral region and being suitable for exciting fluorescent light in the bank note to be checked, measuring with a fluorescence detector and generating a first measured value,
    b) measuring with the fluorescence detector with the illumination switched off and generating a second measured value,
    c) correcting the first measured value generated with the illumination switched on with the second measured value generated with the illumination switched off, and
    d) comparing the corrected measured value with a predefined threshold value.

18. The method according to claim 17, wherein the light-emitting diode is switched on and off periodically.

19. The method according to claim 17, wherein the first measured value generated with the illumination switched on is corrected with the second measured value generated with the illumination switched off by subtracting the second measured value from the first measured value.

20. The method according to claim 17, wherein the first measured value generated with the illumination switched on is corrected with the second measured value generated with the illumination switched off by lock-in amplification of an output signal generated by the fluorescence detector.

21. The method according to claim 17, wherein the corrected measured value or the threshold value is corrected with correction value K which takes account of the change of intensity in the light emitted by the light-emitting diode in the course of the operating lifetime of the light-emitting diode.

22. The method according to claim 21, including the steps:
   measuring at least part of the light emitted by the light-emitting diode with a monitor detector at a first and a later second time with the light-emitting diode switched on and without a bank note to be checked in each case, thereby generating first and second monitor values associated with the measurements at the first and second times in each case, and
   determining correction value K from the first and second monitor values.

23. The method according to claim 17, wherein the method is performed at several places on the bank note to be checked.

24. The method according to claim 23, wherein the measured values measured at several places on the bank note to be checked and corrected are averaged, thereby generating a mean value that is compared with the threshold value.

25. The method according to claim 17, including the steps of
   measuring fluorescent light emitted by the bank note to be checked with the light-emitting diode switched on,
   measuring phosphorescent light emitted by the bank note to be checked with the light-emitting diode switched off, and
   using the measured fluorescent and phosphorescent light of the bank note to be checked for authenticity testing.

* * * * *